United States Patent [19]  
Zier et al.

[11] Patent Number: 4,919,141  
[45] Date of Patent: Apr. 24, 1990

[54] IMPLANTABLE ELECTROCHEMICAL SENSOR

[75] Inventors: Horst D. Zier, Amstetten; Wolfgang Kerner, Dornstadt-Bollingen; Ernst F. Pfeiffer, Ulm, all of Fed. Rep. of Germany

[73] Assignee: Institute für Diabetestechnologie Gemeinnützige Forschungs- und Entwicklungsgesellschaft mbH, Ulm, Fed. Rep. of Germany

[21] Appl. No.: 140,476

[22] Filed: Jan. 4, 1988

[30] Foreign Application Priority Data

Jan. 3, 1987 [DE] Fed. Rep. of Germany ....... 3700119

[51] Int. Cl.$^5$ ................................................. A61B 5/00
[52] U.S. Cl. ..................................... 128/635; 204/403; 204/415; 204/422; 204/435
[58] Field of Search ................. 128/635; 204/403, 415, 204/422, 435

[56] References Cited

U.S. PATENT DOCUMENTS

| 3,542,662 | 11/1970 | Hicks et al. ........................ 204/403 |
| 3,957,613 | 5/1976 | Macur .............................. 204/415 X |
| 4,002,547 | 1/1977 | Neti et al. ........................ 204/435 |
| 4,240,438 | 12/1980 | Updike et al. ....................... 128/635 |
| 4,253,456 | 3/1981 | Schindler et al. . |
| 4,366,033 | 12/1982 | Richter et al. .................. 128/635 X |
| 4,458,686 | 7/1984 | Clark, Jr. .......................... 128/635 |
| 4,627,892 | 12/1986 | Worrell et al. ..................... 204/422 |

FOREIGN PATENT DOCUMENTS

| 0206531 | 12/1986 | European Pat. Off. . |
| 3225871 | 7/1986 | Fed. Rep. of Germany . |
| 2528315 | 12/1983 | France . |
| 0169668 | 10/1982 | Japan ................................. 128/635 |
| 2108675 | 5/1983 | United Kingdom . |
| 2159625 | 12/1985 | United Kingdom . |
| WO86/04223 | 7/1986 | World Int. Prop. O. . |

OTHER PUBLICATIONS

Fischer et al, "A Membrane . . . Fluids", Trans. Am. Soc. Art. Intern. Org., vol. 2B, 1982, pp. 245-248.

Primary Examiner—Lee S. Cohen  
Attorney, Agent, or Firm—Horst M. Kasper

[57] ABSTRACT

The implantable electrochemical sensor for amperometric measurements in body liquids comprises at least one measurement electrode formed as a platinum wire, a reference electrode tubularly surrounding the measurement electrode and possibly made up of several parts and made of stainless steel containing molybdenum as an alloying component. Furthermore, a layer of an immobilized enzyme, such as glucose oxidase, is disposed on the electrodes. The sensor is intended for use for the control of blood sugar and tissue sugar in diabetics and is suitable to be employed in a portable diagnostic and/or therapeutic apparatus.

15 Claims, 5 Drawing Sheets

IMPLANTABLE ELECTROCHEMICAL SENSOR

BACKGROUND OF THE INVENTION

1. Field of the Invention

The invention relates to an implantable sensor for amperometric measurements in body liquids, such as blood or tissue liquid, with a measurement electrode, preferably provided by a platinum or gold wire, and with a reference electrode tubularly surrounding the measurement electrode.

2. Brief Description of the Background of the Invention Including Prior Art

Such sensors are of interest in particular in connection with the control of blood sugar and tissue sugar for diabetics and they are suitable to be employed in a portable diagnostic and/or therapeutic apparatus.

A patient, suffering from the metabolic disease diabetes mellitus, has to balance several times daily his or her blood-sugar level by injection of insulin. In order to be protected against substantial metabolic deviations, in addition, blood-sugar controls are required. The blood-sugar controls require each time a pricking of the finger tip, which represents a substantial burden, in particular for small children and adolescents. On the other hand, the continuously changing metabolic situation of a diabetic person can result in the feared diabetic delayed lesion and late damages, which are caused in particular based on changes of the vessels and a worsening of the oxygen supply to the individual organs.

In order to alleviate the control of blood sugar, electrochemical enzyme sensors have been employed successfully for some time already for determination of blood glucose in vitro. The respective apparatus are however still fairly expensive and heavy in their construction such that they can only be considered for a stationary treatment.

The use of implantable enzyme sensors has already been proposed, where the implantable enzyme sensors are to be employed in connection with portable measurement and evaluation apparatus. A conventional needle-shaped glucose sensor of this kind exhibits a measurement anode consisting of a platinum wire, a reference cathode consisting of silver, and a glass insulator disposed between the measurement anode and the reference cathode, an enzyme layer of an immobilized glucose oxidase disposed on the active electrode surface, as well as a porous membrane of polyurethane covering the enzyme layer. The limiting diffusion currents, measured at a polarization voltage of about 600 millivolts, are from several 100 microamperes to several nanoamperes, depending linearly on the glucose concentration in the presence of $\beta$-D glucose in an electrolytic body liquid. However, in case of in vivo measurements, there eventually occurs a drifting to lower limiting diffusion currents over the course of time which is presumably caused by deposits of fibrin from the tissue and/or blood. This drifting can be compensated in fact by recalibration over certain periods of time. If these recalibrations cannot be performed automatically then, however, in this context, manipulating difficulties occur, which could oppose a wide application of such sensors. This holds the more, since the reference electrode, made of silver and therefore determining the cost, still requires material costs that are too high for such a consumer article. Finally, the data-capturing and data-evaluating apparatus are missing for a practical use of the implantable glucose sensors, which apparatus is sufficiently compact for transportation at or in the body and which are suitable for a long-term battery operation.

SUMMARY OF THE INVENTION

1. Purposes of the Invention

It is an object of the present invention to provide an implantable electrochemical sensor, which can be produced at low-cost material requirements as a mass-produced article for wide application and which, nevertheless, exhibits good biocompatible and electrochemical properties.

It is another object of the invention to provide a light-weight and transportable apparatus for in vivo measurement and surveillance of the component materials of body liquids.

It is yet another object of the present invention to provide for a system which can be carried on a person and providing indications of problems with the blood sugar level.

These and other objects and advantages of the present invention will become evident from the description which follows.

2. Brief Description of the Invention

Experiments with stainless steel as reference electrodes have shown that, in particular in the presence of a molybdenum component of a few weight percent, the glucose-content determinations with a linearity to values of up to 800 mg/dl can be performed in the amperometric measurement with polarization voltages of from 680 to 750 millivolts. The recited stainless steel has proven to be biocompatible to a large extent. During in vivo measurements in subcutaneous tissue of sheep, no substantial decrease of the measurement sensitivity was determined during a measurement duration of four days. The drift in various experiments was a decrease in sensitivity of between 11% and 15% as compared to the initial value. Starting from this, it is disclosed according to the invention that the reference electrode comprises a stainless steel containing molybdenum as an alloying component. Particularly advantageous has proven to be stainless steel with from about 16 to 20 weight-percent chromium, 9 to 13 weight-percent nickel, 1.5 to 4.5% molybdenum, and with at most 0.2 weight-percent carbon, where possibly further alloying components niobium and/or titanium can be present with a weight amount of less than 1 weight-percent. The balance of the steel composition is iron.

The reference electrode is advantageously formed as a thin cannula within which the measurement electrode is embedded in a synthetic resin mass in axial direction with a free end directed to the tip of the cannula, which free end is coated or covered with the enzyme. The cannula tip should then be covered with a membrane, preferably of porous polyurethane, permeable to the body liquid and the glucose dissolved therein as well as to oxygen and which membrane should be impermeable to the enzyme.

As already described, after a longer duration of diabetes, there can occur changes in the vessels which result in an inadequacy and deficiencies of the oxygen supply to the organs and to the tissue. An early recognition of this oxygen deficiency can contribute to the prevention of delayed or late diabetic damages. Furthermore, an oxygen deficiency in the tissue liquid can have the result that systematic deviations occur in the determination of the glucose contents. For these reasons, in particular with diabetics, there exists a need for performing also a surveillance of the oxygen supply to tissue and organs in addition to the blood and tissue sugar measurement.

This measurement can be performed by a simple changing of polarity of the measurement electrode and of the reference electrode while employing the invention sensor. It is particularly advantageous in this context if within the cylinder-shaped reference electrode, there are disposed at least two measurement electrodes parallel to one another, of which only one is covered with the enzyme and which can be connected to a joint measurement line which can be changed in polarity or to measurement lines which are separated from each other.

A particularly good separation between the electrochemical processes within the sensor is achieved by providing at least two reference electrodes, which are electrically insulated against each other, and of which one, in each case, is electrochemically coordinated to one of the measurement electrodes. In this context, the reference electrodes can be made of differing materials, whereby the reference electrode, coordinated to the measurement electrode with enzyme covering, is made of stainless steel with molybdenum component, while the reference electrode, coordinated to the measurement electrode without enzyme covering, can comprise silver or silver/silver chloride. Advantageously, the reference electrodes are formed as partially cylindrical shells, which can be joined to a tubular cannula and which are connected to each other at their seam by an insulating synthetic resin.

The measurement electrodes and the reference electrodes are connected in pairs to the inputs of at least one measurement amplifier. Various groups of measurement electrodes and reference electrodes can be applied with a polarization voltage of opposite polarity. In case of a combination sensor for the glucose and oxygen measurement, the platinum measurement electrode, covered with glucose oxidase, and the enzyme-free platinum measurement electrode, exhibit, as compared to their reference electrodes made of stainless steel or, respectively, silver, polarization voltages of opposite polarity of preferably 600 to 750 millivolts.

The implantable sensor according to the invention is preferably employed in connection with a diagnostic apparatus for surveillance of the materials contained in body liquids, such as β-D glucose and/or oxygen in blood or tissue liquid. Such an apparatus comprises a measurement amplifier which can receive the sensor signal as well as a circuit containing an analog to digital converter for the evaluation of the output signal of the measurement amplifier. Under the conditions that there is a linear connection between the measurement current and the material concentration to be determined, a simple calibration is possible by applying a reference potential in a stepless manner at the input of the analog to digital converter, under adaptation to preset values of a test medium. The digital measurement value calibrated in this manner can be stored in predetermined time intervals in a write-read memory storage. In order to determine the metabolic situation of a patient, these values can be read out at larger time intervals via an interface and can be transferred to a printer and/or an external computer. If the measurement and storage circuit is formed battery-operated, in an energy-saving CMOS technique, then it can be placed easily in a transportable apparatus, which can be carried along on the body of the patient. The momentary measurement and operating values can be read on a liquid crystal display.

According to a further advantageous embodiment of this invention, there can further be provided a microprocessor, which contains a program for the control of an insulin pump depending on the deviation of the blood or tissue sugar measurement values from at least one set point value or set point value course. The insulin amount values, determined by the program, can be stored together with the glucose measurement values in a write-read memory storage and can be read out via an interface. Thus, a portable apparatus is obtained, which is suitable for the automatic control of the glucose metabolism of a patient. Based on the complete capture of data, the metabolic situation of the patient is in addition surveilled in short time intervals such that possible disturbances can be observed and, if required, be corrected by the medical doctor or can be treated.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing, in which are shown several of the various possible embodiments of the present invention.

DESCRIPTION OF INVENTION AND PREFERRED EMBODIMENT

Figure 3:
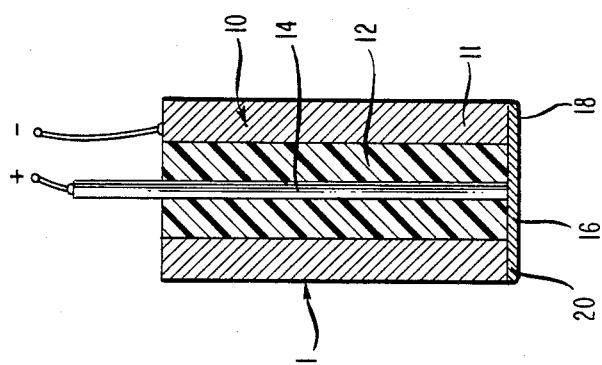
FIG. 3 is a vertical sectional view of a combination sensor with two separate partial cells.

The implantable sensor for amperometric measurements in body liquids, such as blood or tissue liquid, with a measurement electrode is preferably formed as a platinum or gold wire, a reference electrode tubularly surrounding the measurement electrode, as well as a layer of an immobilized enzyme disposed on the electrodes, such as glucose oxidase. The tubular reference electrode 11 comprises a stainless steel containing molybdenum as an alloy component.

The reference electrode 11 can comprise a steel with 16 to 20 weight-percent chromium, 9 to 13 weight-percent nickel, 1.5 to 4.5 weight-percent molybdenum, and at most 0.2 weight-percent carbon. The molybdenum part can amount from 1.8 to 2.3 weight-percent. The reference electrode 11 can contain as further alloy components niobium and/or titanium of a weight-percentage of less than about 1%.

Preferably, the reference electrode 11, 11' is formed as a cannula 10. The measurement electrode 14, 14' can be embedded in a synthetic resin filler 12 in an axial direction with an end directed toward the pinpoint 16 of the cannula and with a free end covered with the enzyme layer 20. The tip of the cannula can be covered with a membrane 18 which can be permeable to the body liquid and the glucose dissolved therein as well as to oxygen and which membrane 18 can be impermeable to the enzyme layer 20. The membrane 18 preferably consists of porous polyurethane.

Preferably, at least two measurement electrodes 14, 14', directed in parallel to each other, are disposed in the cannula 10. Preferably, only one or part of one measurement electrode 14 is covered with the enzyme layer 20. The measurement electrodes 14, 14' can be connected to a joint measurement line. Preferably, at least two groups of the measurement electrodes 14, 14' are connected to measurement lines separated from each other.

The pinpoint 16 of the cannula with the measurement electrode 14, 14' and at least one part of the jacket face of the reference electrode 11, 11', forming the cannula 10, can be covered with a connected oxygen-permeable membrane 18.

Preferably, at least two reference electrodes 11, 11', electrically insulated against each other, are provided, of which reference electrodes, in each case, one is coordinated electrochemically to a measurement electrode 14, 14' or to a measurement electrode group.

Preferably, at least one reference electrode 11 comprises stainless steel with molybdenum as an alloying component, and at least one reference electrode 11', coordinated to a measurement electrode 14' without enzyme coating, comprises silver or silver/silver chloride.

The reference electrodes 11, 11' can comprise partially cylindrical shells which supplement themselves to a tube-shaped cannula 10 and which can be connected to each other at their seam by way of an insulating synthetic resin.

The measurement electrodes 14, 14' and the reference electrodes 11, 11' can be applied in pairs to the input of at least one measurement amplifier 3.

Different groups of measurement electrodes 14, 14' and reference electrodes 11, 11' can be applied with a polarization voltage of opposite polarity.

The groups of measurement electrodes 14, 14' and of reference electrodes 11, 11' of opposite polarity can be applied to the field effect transistor (FET) inputs of a measurement amplifier 3 via a switch 40 changing the polarity of the polarization voltage.

The groups of measurement electrodes 14, 14' and of reference electrodes 11, 11' of opposite polarity can be applied to the field effect transistor (FET) inputs of a measurement amplifier 3, 3' in each case. The outputs of the measurement amplifiers 3, 3' can be applied switchable to an evaluation circuit 38.

The enzyme-coated measurement electrode 14 can be provided with a positive polarization voltage and the enzyme-free measurement electrode 14' can be provided with a negative polarization voltage versus the respective reference electrodes 11, 11'.

In the case of a combination sensor 1 for the glucose and oxygen measurement, the platinum measurement electrode 14 coated with glucose oxidase 20 and the enzyme-free platinum measurement electrode 14' can exhibit polarization voltages of from about 600 to 750 millivolts of opposite polarity versus their reference electrodes 11, 11' of stainless steel and/or silver.

An apparatus for in vivo measurement and surveillance of component materials in body liquids, such as $\beta$-D-glucose and/or oxygen in blood or tissue liquids, comprises an implantable sensor, in particular one as described above. A measurement amplifier can be provided with a sensor signal as well as with a circuit containing an analog to digital converter for evaluation of the output signal of the measurement amplifier. At least one reference potential for calibration of the analog output signal of the measurement amplifier 3 can be steplessly adjusted at the input of the analog to digital converter 50 under adaptation of predetermined values of a test medium. The digital measurement values, calibrated in this manner, can be stored in a read-write memory storage 60 at predetermined time intervals. The content of the read-write memory storage 60 can be read at larger time intervals over an interface 70 and can be transferred to a printer and/or an external computer. The measurement and storage circuit can be formed as a transportable battery-operated arrangement with a current-saving CMOS technique.

In addition a liquid crystal display 52 can be provided for representing the momentary measurement and operating values.

The input connection terminals of the measurement amplifier 3, which can be applied with a bias voltage and which can be connected with the electrodes 11, 11', 14, 14' of the electrochemical sensor 1, can be changed in polarity.

There can be provided two measurement amplifiers 3, 3', connected with two different partial cells of the electrochemical sensor. The inputs of the measurement amplifiers 3, 3' can receive independent from each other an adjustable bias voltage. The output voltages of the measurement amplifiers 3, 3' can be connected selectively with an analog input of an analog to digital converter 50.

Preferably, the evaluation circuit 38 comprises a microprocessor 80 which can receive the measurement and/or operating values of the apparatus. The microprocessor 80 can initiate alarm signals and/or the feeding of pharmaceutically active agents depending on the conformity and/or deviation of the momentary measurement values with, respectively of, at least one set point value and/or at least one set point value course and/or depending on the operating values.

The microprocessor 80 can include a program for controlling of an insulin pump 82, depending on the deviation of the measured blood or tissue sugar values of at least one set point or set point course. The insulin amount values, determined by the program, together with the glucose measurement values, can be stored in a write-read memory storage 60 and can be read out via the interface.

Figure 2:
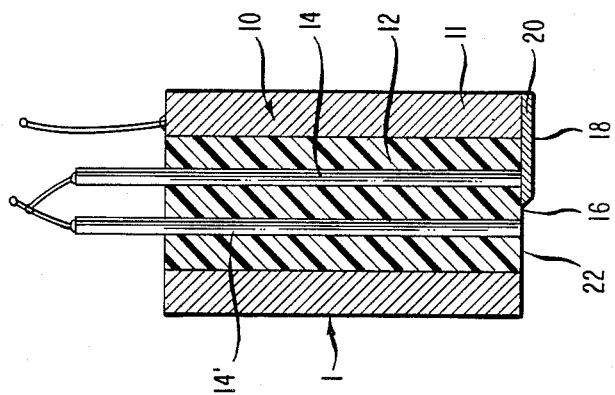
FIG. 2 is a vertical sectional view of a combination sensor with two measurement electrodes and a joint reference electrode.
Figure 1:
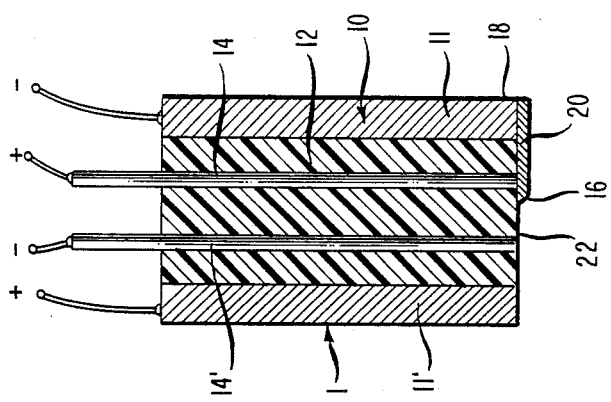
FIG. 1 is a vertical sectional view of an enzyme sensor with a measurement electrode and a reference electrode.

The electrochemical enzyme sensors 1 illustrated on an enlarged scale in FIGS. 1 to 3 are intended for in vivo measurements in the human or animal bodies. They comprise essentially a thin cylindrical tube-shaped cannula 10 made of metal, which contains an insulating epoxy resin filler 12 as well as one or two axially directed measurement electrodes 14, 14'. The metallic tube jacket forms at the same time the reference electrode 11' of the electrochemical sensor.

The active measurement location of the sensor is disposed at its front face 16, at which front face the measurement electrode 14 protrudes from the insulated epoxy resin filler 12 and is covered with a porous, semipermeable, biocompatible membrane 18 and an enzyme layer 20 enclosed within the membrane.

The measurement electrodes 14, 14' preferably comprise platinum or gold, whereas the reference electrodes 11 of the enzyme cells are made of stainless steel with molybdenum as an alloying component. In the case of FIG. 3, two reference electrodes 11, 11', formed as cylindrical half-shells, are provided. The reference electrodes 11, 11' are connected to each other with a plastic insulation, not illustrated, under formation of the tube-shaped cannula 10. The reference electrode 11 corresponding to the enzyme cell, is again made out of stainless steel with molybdenum component, whereas the reference electrode 11' corresponding to the enzyme-free partial cell is preferably made of silver.

The cells can have a substantially cylindrical symmetry where the base line of the cylinder is preferably a circle or an ellipsis. The center of the base line preferably coincides with the center of gravity of the measurement electrode or electrodes.

The needle-shaped sensor 1 has a diameter of about 0.5 to 1.0 mm, where the measurement electrodes 14, 14' exhibit a diameter of 0.15 to 0.2 mm. The tube-shaped cannula 10 can have a length of from about 1 to 3 mm. The tube-shaped cannula 10, containing a platinum wire or platinum wires, is filled with liquid epoxy resin filler 12 containing a hardener and is maintained in its position until the resin has hardened. Then, the front-side end face 16 is freed from the protruding epoxy resin and is abraded while freeing the wire ends. Then, the sensor pinpoint is dipped into a suspension of glucose oxidase 20 in ethanol acetone and is air-dried. By dipping and submerging into a solution of polyurethane dissolved in tetrahydrofuran, followed by air-drying, the semipermeable polyurethane membrane 18 is formed. One of the platinum electrodes 14' and a part of the reference electrode 11' are, after the covering with the enzyme, again freed of the enzyme, or are provided with a covering to be subsequently removed before the covering with the enzyme layer such that an enzyme-free region 22 is generated in the combination sensors illustrated in FIGS. 2 and 3.

Figure 5:
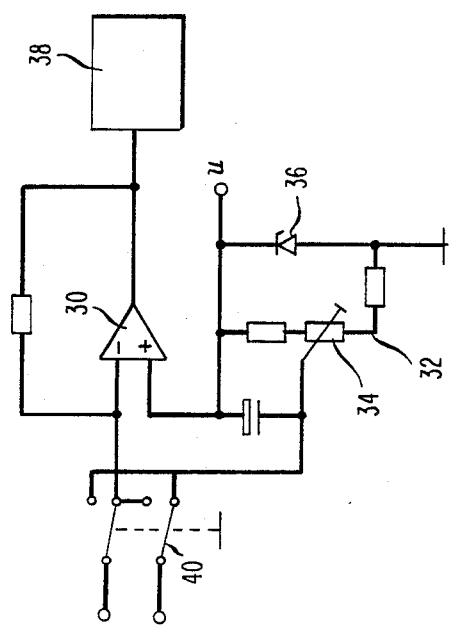
FIG. 5 is a schematic diagram of a measurement circuit for a combination sensor according to FIG. 2.
Figure 4:
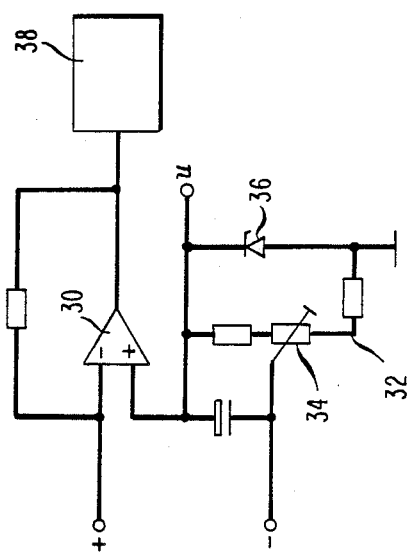
FIG. 4 is a schematic diagram of a measurement circuit for the enzyme sensor according to FIG. 1.
Figure 6:
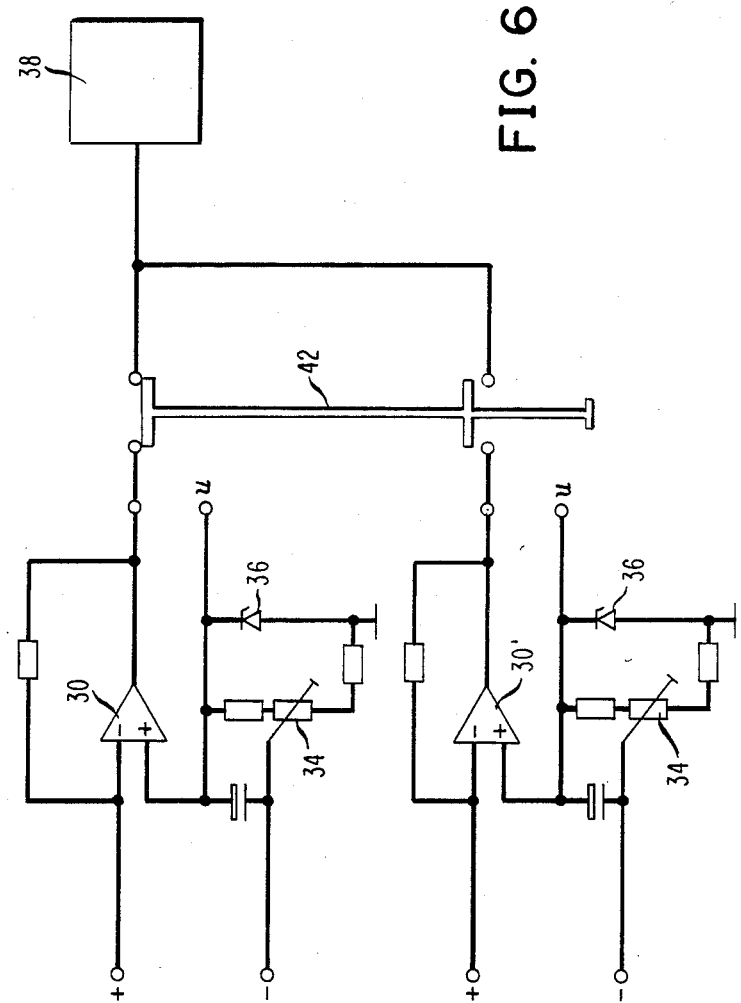
FIG. 6 is a schematic diagram of a measurement circuit for a combination sensor according to FIG. 3.

The measurement and amplifier circuits 3, containing field-effect-transistor FET operational amplifiers 30, are illustrated in FIGS. 4 to 6. The sensors according to FIGS. 1 to 3 can be connected to the measurement and amplifier circuits 3 as follows.

The measurement circuit according to FIG. 4 is intended for connection of the enzyme electrode according to FIG. 1. The measurement electrode 14 can be a platinum anode (+) which is applied to the inverting input of the operational amplifier 30, while the stainless steel reference electrode 11 (−) is applied with a negative bias voltage, adjustable via a potentiometer 34, at the voltage divider circuit 32 to the non-inverting input of the operational amplifier 30. The set bias voltage is stabilized via a Zener diode 36. The measurement signal of an evaluation circuit 38, connected to the output of the measurement amplifier 3, is further processed in the manner illustrated in detail below.

The body liquid serves as an electrolyte in the performance of the measurement, into which body liquid the electrochemical sensor is immersed, for example, by implantation. β-D glucose present in the body liquid is oxidized in the presence of oxygen into D-glucose lactone under release of hydrogen peroxide $H_2O_0$ in the glucose sensor, which contains glucose oxidase as enzyme 20:

The rate of formation of $H_2O_2$ can be measured in the electrochemical cell as a limiting diffusion current based on the following reaction at the platinum electrode:

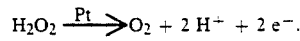

The indicated reaction preferably occurs in a cell with a platinum anode and a stainless steel cathode at a polarization voltage of 680 to 750 millivolts. The measurable limiting diffusion current is, over wide ranges, proportional to the glucose concentration in the body liquid. The oxygen present in the tissue or in the blood is sufficient for the reaction, in particular since the oxygen used up in the glucose transformation is recovered during the conversion of $H_2O_2$ at the platinum reference electrode 11 and is again fed back, at least partially, to the body liquid.

In principle, it is possible to operate the sensor illustrated in FIG. 1 in connection with one of the measurement circuits also with an opposite polarization voltage, i.e. with the platinum wire as a cathode and the stainless steel tube as an anode. In this manner, one obtains initially $H_2O_2$ and subsequently $H_2O$ at the measurement electrode by a reduction of the oxygen contained in the body liquid according to the following reaction equations:

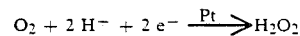

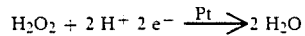

The plateau voltage for the measurement of the limiting diffusion current of these two reaction stages is from about −600 to −700 millivolts. Thus, the limiting diffusion current at a constant voltage between measurement cathode and reference anode is taken as a measure for the oxygen $O_2$ molecules reaching the cathode over a unit time period and is employed for measuring the oxygen partial pressure in the body liquid. The sensor described according to FIGS. 1 to 3 can be employed by a simple changing of polarity of the measurement electrode and of the reference electrode for measuring and surveillance of two different measurement substances, i.e. of β-D-glucose and oxygen.

The sensor illustrated in FIG. 1, however, is not optimum as a combination sensor insofar as, in the case of a switching to an oxygen sensor, the oxygen would have to diffuse through the enzyme layer 20, which could result in a lowering of the limiting diffusion current and thus a lowering of sensitivity. In order to avoid this disadvantage, two measurement electrodes 14, 14' are provided according to FIGS. 2 and 3, where only one is covered in its active region with the enzyme reaction agent layer 20, while the other measurement electrode is at this location free from enzymes. The enzyme partial cell thus exhibits, in case of a corresponding switching in the measurement electrodes in FIGS. 5 and 6, a measurement electrode 14 made of platinum, switched as an anode, and a reference electrode 11' made of stainless steel, switched as a cathode, while the oxygen partial cell comprises a platinum measurement electrode 14', switched as a cathode, and a reference electrode 11, switched as an anode. A joint reference electrode 11, 11' of stainless steel is provided in the case of FIG. 2, which reference electrode 11, 11' can be switched from case to case via the switch 40 of the measurement circuit according to FIG. 5 as a cathode and anode while, in the case of FIG. 3, two reference electrodes 11, 11', formed as cylindrical half shells and electrically insulated against each other, are provided, where the enzyme partial cell is switched as a reference electrode 11 operating as a cathode and is preferably made out of stainless steel, while the $O_2$ partial cell is switched as a reference electrode 11' operating as an anode and is preferably made of silver.

The electrodes 11, 11', 14, 14' are applied to measurement channels 30, 30' independent of each other, which measurement channels 30, 30' can be connected selective and alternatingly with the evaluation circuit 38 via a switch 42. Thus, upon switching, a change in polarization within the cells is avoided such that the measurements at the two partial cells can be performed in quick sequence.

The glucose sensors described with their measurement circuits can be employed in connection with a portable diagnostic apparatus (FIG. 7) or with a combined diagnostic and therapeutic apparatus (FIG. 8) as an evaluation circuit 38.

The fact that a linear connection exists between the substance concentration (glucose or, respectively, oxygen) present in the electrolyte and the measured limiting diffusion current, can be employed to perform the calibration of the apparatus in a relatively simply way at an analog measurement amplifier by a stepless adjustment of the zero point and of the degree of amplification (full scale).

The diagnostic apparatus illustrated in FIG. 7 in a block circuit diagram is essentially constructed as follows:

The analog data present at the output of the measurement amplifier 3 are converted in a analog to digital converter 50 into digital values and are displayed in this way by a liquid crystal display 52 and are intermediately stored in a parallel memory storage 54. The intermediately stored data are written at predetermined time intervals into a write-read memory storage 60 which are determined by a quartz timer 56 and an externally adjustable time selection apparatus 58. This process is initiated via a write control device 62, which controls both an address counter 64 as well as the write input and the chip-select input of the write-read memory storage 60. The write-read memory storage 60 is formed as a current-saving CMOS-RAM, buffered by battery 66, such that the data stored are maintained even in case of a turned-off apparatus. The content of the write-read memory storage can be read out via write-out control 68, which can be controlled via an externally connectable interface 70 to the output register and can be transferred from the output register to an external computer or immediately to a printer. By employing modern semiconductor components, the complete circuit can be placed onto a single printed circuitboard such that a small light-weight apparatus can be provided for capturing the measurement data and for storing the measurement data. The small, light-weight apparatus can be applied directly to the body of the patient without disturbing the operational sequence. In case of a further miniaturization of the components, the apparatus can be reduced in its dimensions to such a degree that it can be carried like a wristwatch on the arm.

Figure 7:
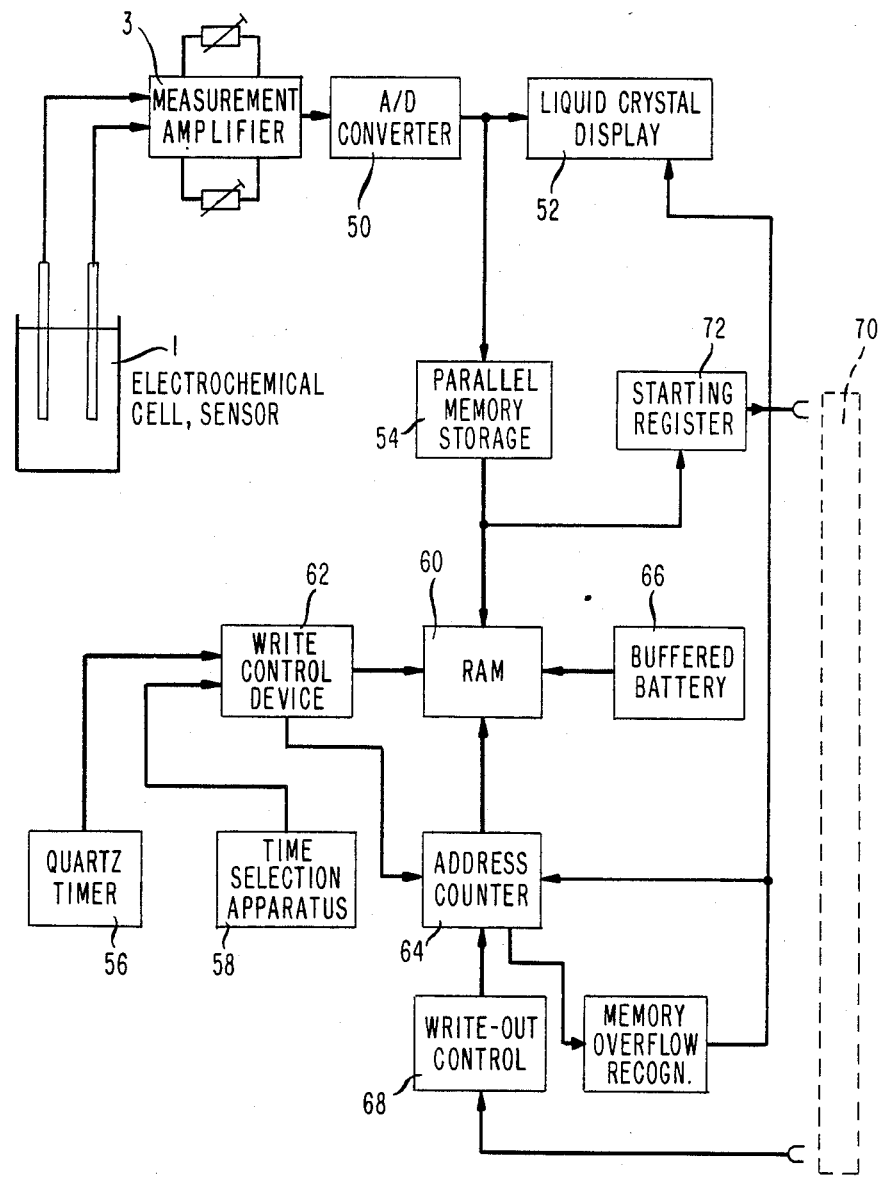
FIG. 7 is a block circuit diagram of a diagnostic apparatus.
Figure 8:
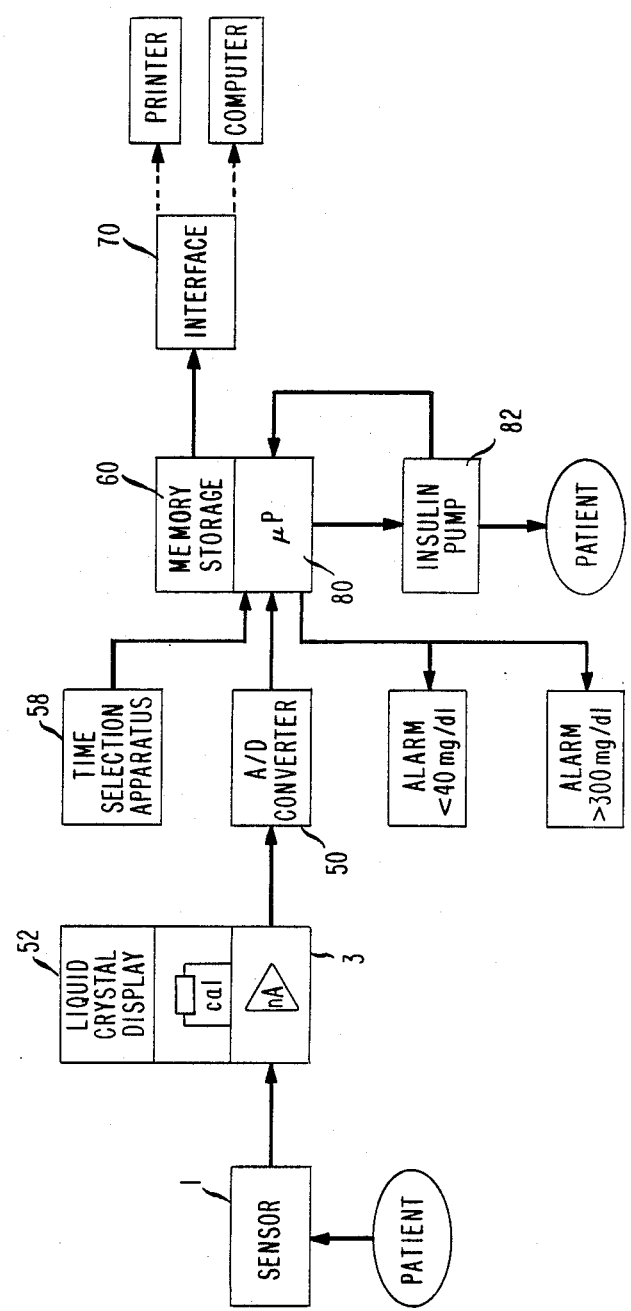
FIG. 8 is a block circuit diagram of an automatic diagnostic and therapeutic apparatus.

The diagnostic and therapeutic apparatus illustrated in FIG. 8 by way of a schematic block diagram is a further embodiment of the diagnostic apparatus of FIG. 7. It contains in addition a microprocessor 80 for evaluation of the received digital measurement values. In order to protect a diabetic from dangerously low sugar values and dangerously high sugar values, in case of a lowering of the blood-sugar value to less than 40 mg/dl, and in case of exceeding of a value of 300 mg/dl, an alarm signal is initiated by the microprocessor 80. Furthermore, an insulin pump 82 can be controlled via a microprocessor program depending on the measured blood or tissue sugar values and under taking into consideration of various patient parameters to be entered by the medical doctor. The insulin pump employs a step motor for feeding an insulin amount, calculated by the microprocessor in each case, to the patient via a needle catheter disposed in the tissue of the abdomen.

The actual glucose values and the insulin amounts provided by the insulin pump 82 are stored at set time intervals in the write-read memory storage and these values can be read out from time to time via an externally connectable interface 70 from the storage and can be printed or can be further evaluated in a computer for checking the setting of the metabolism of the patient.

The microprocessor employed according to the invention can be any one of many commercial microprocessors available, such as the Intel Chip 8086, the Motorola Chip 68000, as well as their predecessor and successor models. The microprocessor can be programmed in its assembly language as well as with compiled programs of a higher language.

The programming can be performed such that a comparison is performed between an observed time sequence of glucose and oxygen values with preset oxygen or glucose function values having a certain relationship or time sequence and that, based on the result of such comparison, certain actions are taken and final function-control elements are initiated.

It will be understood that each of the elements described above, or two or more together, may also find a useful application in other types of sensors differing from the types described above.

While the invention has been illustrated and described as embodied in the context of an implantable electrochemical sensor for amperometric measurements in body liquids, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. Implantable sensor for amperometric measurements in body liquids, such as blood or tissue liquid, comprising
a measurement electrode;
a reference electrode tubularly surrounding the measurement electrode and made of a stainless steel containing molybdenum as an alloy component; and a layer of an immobilized enzyme being disposed on at least one end of the electrodes, wherein said at least one end is adapted for insertion into a body liquid.

2. Sensor according to claim 1, wherein the reference electrode comprises a steel with 16 to 20 weight-percent chromium, 9 to 13 weight-percent nickel, 1.5 to 4.5 weight-percent molybdenum, and at most 0.2 weight-percent carbon.

3. Sensor according to claim 1, wherein the molybdenum component amounts from 1.8 to 2.3 weight-percent.

4. Sensor according to claim 1, wherein the reference electrode contains as further alloy components niobium and/or titanium of a weight-percentage of less than about 1%.

5. Sensor according to claim 1, wherein the reference electrode is formed as a cannula and where the measurement electrode is embedded in a synthetic resin in an axial direction with the at least one end directed toward a tip of the cannula, and wherein a pinpoint of the cannula and said at least one end of the measurement electrode is covered with a membrane which is permeable to the body liquid and the glucose dissolved therein as well as to oxygen and which membrane is impermeable to the enzyme and which membrane consists of porous polyurethane.

6. Sensor according to claim 1, wherein the reference electrode is formed as a cannula with a pinpoint at the at least one end adapted for insertion into a body liquid, wherein the pinpoint of the cannula is covered with a membrane which is permeable to the body liquid and the glucose dissolved therein as well as to oxygen and which membrane is impermeable to the enzyme and which membrane consists of porous polyurethane, and wherein the measurement electrode is embedded in a synthetic resin in an axial direction with the at least one end directed toward the pinpoint of the cannula and covered with the enzyme.

7. Sensor according to claim 6, wherein at least two measurement electrodes, directed in parallel to each other, are disposed in the cannula.

8. Sensor according to claim 7, wherein the one end of the one measurement electrode is covered with the enzyme and wherein the enzyme is glucose oxidase.

9. Sensor according to claim 8, wherein the measurement electrodes are connected to a joint measurement line and wherein the measurement electrodes are formed by a platinum wire.

10. Sensor according to claim 8, wherein the measurement electrodes (14, 14') are connected to measurement lines separated from each other and wherein the measurement electrodes are formed by a gold wire.

11. Sensor according to claim 7, wherein the pinpoint of the cannula the at least one end of the measurement electrode and at least one part of a jacket face of the reference electrode forming the cannula are covered with a connected oxygen-permeable membrane.

12. Sensor according to claim 7, wherein at least two reference electrodes, electrically insulated against each other, are provided, of which reference electrodes, in each case, one is coordinated electrochemically to one or more measurement electrodes.

13. Sensor according to claim 12, wherein only one of the measurement electrodes is covered with enzyme, wherein at least one reference electrode comprises stainless steel with molybdenum as an alloying component, and wherein at least one reference electrode coordinated to a measurement electrode without enzyme coating comprises a material selected from the group consisting of silver, silver/silver chloride and mixtures thereof.

14. Sensor according to claim 12, wherein the reference electrodes comprise partially cylindrical shells having a seam which shells supplement themselves to a tube-shaped cannula and which are connected to each other at their seam by way of an insulating synthetic resin.

15. Sensor according to claim 7, wherein the at least one end of only one of the measurement electrodes is fully or partially covered with the enzyme and wherein the enzyme is glucose oxidase.

* * * * *